United States Patent
Shin et al.

(10) Patent No.: US 11,881,558 B2
(45) Date of Patent: Jan. 23, 2024

(54) ELECTROLYTES FOR LITHIUM-CONTAINING BATTERY CELLS

(71) Applicant: Apple Inc., Cupertino, CA (US)

(72) Inventors: Woo Cheol Shin, San Jose, CA (US); Soonho Ahn, San Jose, CA (US)

(73) Assignee: Apple Inc., Cupertino, CA (US)

( * ) Notice: Subject to any disclaimer, the term of this patent is extended or adjusted under 35 U.S.C. 154(b) by 229 days.

(21) Appl. No.: 16/738,883

(22) Filed: Jan. 9, 2020

(65) Prior Publication Data

US 2021/0218061 A1 Jul. 15, 2021

(51) Int. Cl.

| | |
|---|---|
| *H01M 10/0568* | (2010.01) |
| *H01M 10/0525* | (2010.01) |
| *H01M 10/0569* | (2010.01) |
| *C07C 25/13* | (2006.01) |
| *C07C 25/18* | (2006.01) |
| *C07C 25/22* | (2006.01) |
| *H01M 10/0567* | (2010.01) |

(52) U.S. Cl.
CPC ......... *H01M 10/0568* (2013.01); *C07C 25/13* (2013.01); *C07C 25/18* (2013.01); *C07C 25/22* (2013.01); *H01M 10/0525* (2013.01); *H01M 10/0567* (2013.01); *H01M 10/0569* (2013.01); *H01M 2300/0028* (2013.01)

(58) Field of Classification Search
None
See application file for complete search history.

(56) References Cited

U.S. PATENT DOCUMENTS

| | | | | |
|---|---|---|---|---|
| 2004/0214091 | A1* | 10/2004 | Lim | H01M 10/052 429/340 |
| 2008/0241687 | A1* | 10/2008 | Ishii | H01M 4/136 429/246 |
| 2010/0035146 | A1* | 2/2010 | Fujii | H01M 10/0525 429/188 |
| 2011/0305937 | A1* | 12/2011 | Kim | H01M 50/411 429/188 |
| 2012/0060360 | A1* | 3/2012 | Liu | H01M 10/0525 29/623.2 |
| 2012/0115068 | A1* | 5/2012 | Nakanishi | H01M 12/06 429/498 |
| 2012/0164542 | A1* | 6/2012 | Iwaya | H01M 10/052 252/62.2 |
| 2014/0093783 | A1* | 4/2014 | Lamanna | H01M 10/0565 429/188 |
| 2014/0186696 | A1* | 7/2014 | Onagi | H01M 4/587 429/188 |
| 2015/0288029 | A1* | 10/2015 | Lv | H01M 4/525 429/200 |
| 2016/0211551 | A1* | 7/2016 | Miyasato | H01M 10/0567 |
| 2018/0251681 | A1* | 9/2018 | Zhang | H01M 10/0567 |
| 2018/0269528 | A1* | 9/2018 | Zhang | H01M 4/131 |
| 2019/0198933 | A1* | 6/2019 | Newhouse | H01M 4/13 |
| 2019/0260082 | A1* | 8/2019 | Yamamoto | H01M 10/0569 |

OTHER PUBLICATIONS

Yamada, Yuki et al., "Advances and Issues in Developing Salt-Concentrated Battery Electrolytes." Nature Energy, Review Article, vol. 4, Apr. 2019, pp. 269-280.
Beyene, Tamene Tadesse et al., "Concentrated Dual-Salt Electrolyte to Stabilize Li Metal and Increase Cycle Life of Anode Free Li-Metal Batteries." Journal of the Electrochemical Society, vol. 166, Issue 8, 2019, 17 pages.
Ravikumar, Bharath et al., "Effect of Salt Concentration on Properties of Lithium Ion Battery Electrolytes: A Molecular Dynamics Study." The Journal of Physical Chemistry, J. Phys. Chem. C 2018, 122, pp. 8173-8181.
Haregewoin, Atetegeb Meazah et al., "Electrolyte Additives for Lithium Ion Battery Electrodes: Progress and Perspectives." Energy & Environmental Science, May 2016, 35 pages.
Ren, Xiaodi et al., "Localized High-Concentration Sulfone Electrolytes for High-Efficiency Lithium-Metal Batteries." Cell Press, Chem 4, pp. 1877-1892, Aug. 9, 2018.
Smiatek, Jens et al., "Properties of Ion Complexes and Their Impact on Charge Transport in Organic Solvent-Based Electrolyte Solutions for Lithium Batteries: Insights from a Theoretical Perspective." Batteries, 2018, 4, 62; doi:10.3390/batteries4040062. 34 pages.
Sharova, Varvara et al., "Comparative Study of Imide-Based Li Salts as Electrolyte Additives for Li-ion Batteries." Journal of Power Sources, 375, 2018, pp. 43-52.

* cited by examiner

*Primary Examiner* — Anca Eoff
(74) *Attorney, Agent, or Firm* — Kilpatrick Townsend and Stockton LLP

(57) ABSTRACT

An electrolyte for a lithium-containing battery cell is described. The electrolyte includes a solvent having at least one carbonate ester, and at least one lithium salt having a concentration ranging from 3 mol/liter to 15 mol/liter in the solvent. The electrolyte also includes a diluent that includes an aromatic fluorocarbon. In some embodiments, the solution of the at least one lithium salt and the solvent is a supersaturated solution for at least some operating temperatures of the battery cell. Also described are lithium-containing battery cells that include a positive electrode, a negative electrode, and the electrolyte.

20 Claims, 8 Drawing Sheets

ELECTROLYTES FOR LITHIUM-CONTAINING BATTERY CELLS

TECHNICAL FIELD

The present technology relates to electrolytes incorporated into secondary battery cells. More specifically, the present technology relates to diluted concentrated electrolytes that include both a concentrated active salt in a solvent and a diluent.

BACKGROUND

Conventional electrolytes for lithium-ion battery cells typically include an inorganic lithium salt, often lithium hexafluorophosphate, concentrated to 1-2 moles/liter in a carbonate solvent. These conventional electrolytes have been in use for years due to their relatively inexpensive components and the predictability of their performance. However, these conventional electrolytes have a number of shortcomings that are increasingly difficult to ignore with the proliferation of battery-powered electronic devices that require economical, safe electric power over a high number of recharging cycles. These shortcomings include the release of gases such as carbon dioxide and volatile organic compounds that can swell the battery cell and, in worst-case scenarios, lead to fires and explosions. Thus, efforts are underway to develop electrolytes for lithium-ion battery cells that have a significantly reduced volatility and flammability compared to conventional electrolytes.

One approach to reducing the volatility and flammability of the electrolyte is to concentrate the lithium salt in the electrolyte above the conventional 1-2 mole/liter range. As shown in FIG. 1, the lithium salt concentrations in conventional electrolytes leave a lot of excess free solvent available to volatilize and react with other battery components such as the battery cell's electrodes. In contrast, when the lithium salt is more concentrated in the electrolyte, there are fewer free solvent molecules present because more are tied up in solvent aggregates with the ions of the lithium salt as shown in FIG. 2. Because aggregated solvent is much less likely than free solvent to volatilize and react with other battery components, concentrated electrolytes are less volatile and less flammable than less-concentrated, conventional electrolytes.

Unfortunately, concentrated electrolytes have their own shortcomings that need to be addressed before they can be adopted on a commercial scale. These shortcomings include the increased cost of the electrolyte when the amount of lithium salts needed are greatly in excess of what is required for conventional electrolytes. They also include the decrease in lithium-ion conductivity caused by the increase in viscosity that occurs when the salt becomes more concentrated in the electrolyte. The lower conductivity of the electrolyte increases the electrical resistance of the battery cell, which in turn increases the cell's internal electrical resistance and reduces the cell's rate capability. These and other shortcomings of concentrated electrolytes have to be addressed before they can be adopted on a commercial scale to provide safe, long-lasting lithium-ion battery cells for electronic devices and other applications.

BRIEF DESCRIPTION OF THE DRAWINGS

A further understanding of the nature and advantages of the disclosed embodiments may be realized by reference to the remaining portions of the specification and the drawings.

Several of the figures are included as schematics. It is to be understood that the figures are for illustrative purposes, and are not to be considered of scale unless specifically stated to be of scale. Additionally, as schematics, the figures are provided to aid comprehension and may not include all aspects or information compared to realistic representations, and may include exaggerated material for illustrative purposes.

In the figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

Figure 1:
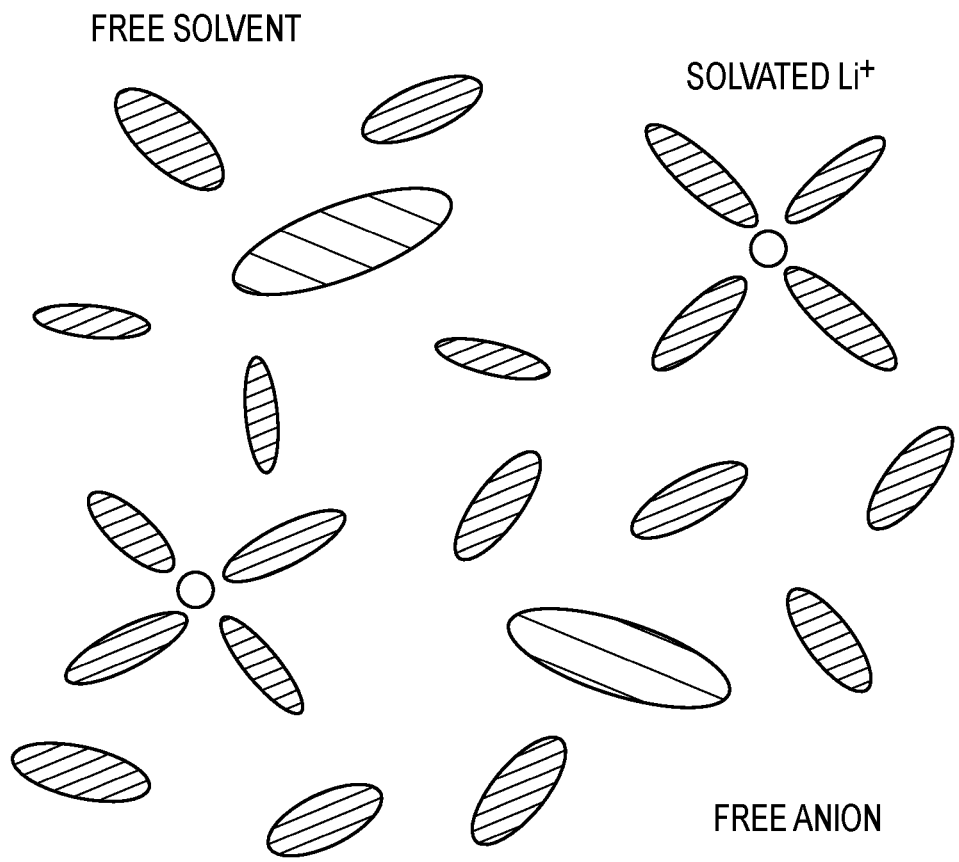
FIG. 1 shows a simplified schematic of free solvent and solvated ions from a lithium salt in a conventional electrolyte.
Figure 2:
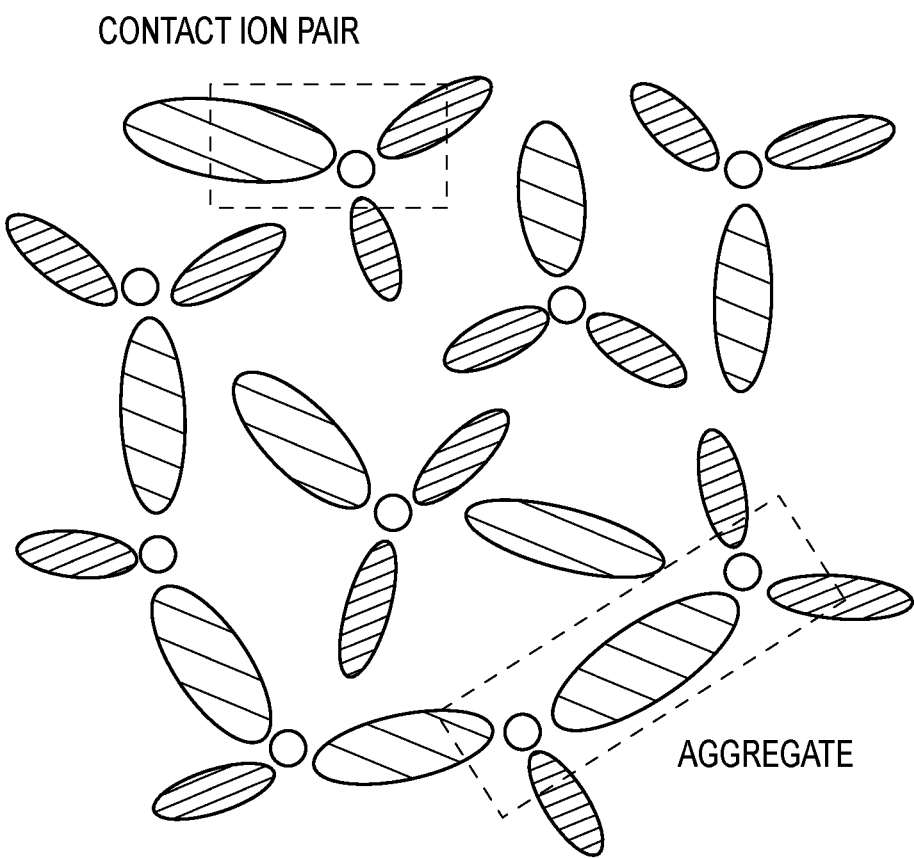
FIG. 2 shows a simplified schematic of solvent-ion aggregates in an electrolyte having a concentrated lithium-containing salt.
Figure 3:
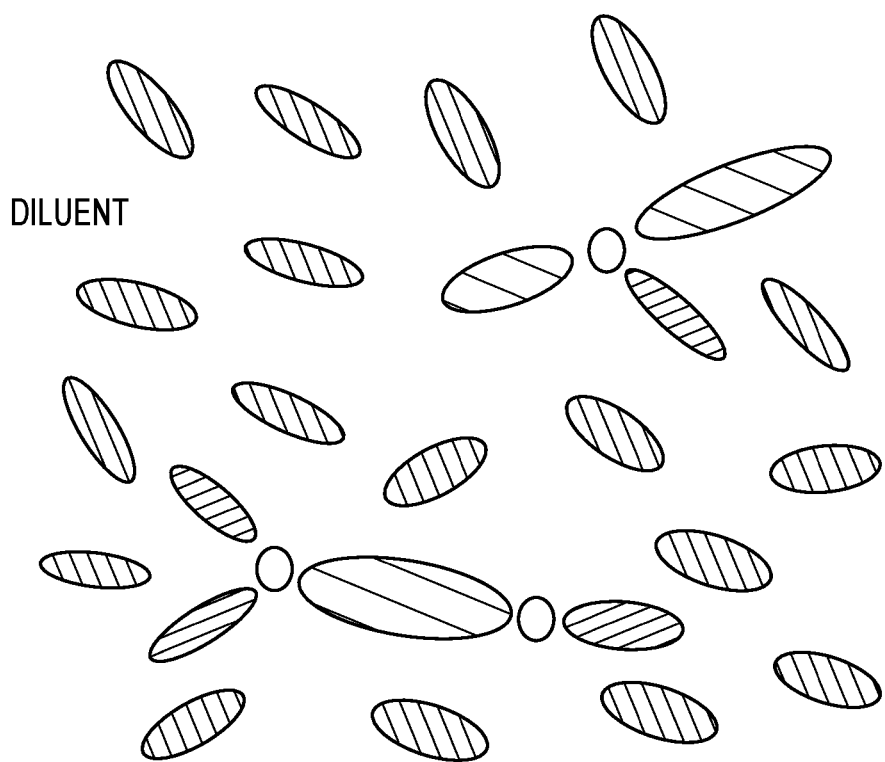
FIG. 3 shows a simplified schematic of dispersed solvent-ion aggregates surrounded by diluent in a diluted concentrated electrolyte according to present embodiments.

The present technology includes diluted concentrated electrolytes that can be incorporated into battery cells. In diluted concentrated electrolytes, one or more concentrated active salts dissolved in a solvent to concentrations greater than 1 mole/liter (e.g., greater than 3 moles/liter, greater than 5 moles/liter, etc.). In some embodiments, the concentrated active salt is supersaturated in the solvent and has a higher concentration than the conventional saturation concentration for the salt in the solvent at that temperature. The electrolyte further includes a diluent that disperses the concentrate of the active salt and solvent into localized regions of highly concentrated active salt throughout the electrolyte as shown in FIG. 3. The high concentrations of active salt in these localized regions integrates almost all the surrounding solvent molecules into coordination complexes, and significantly reduces the amount of free solvent in the electrolyte. The reduction in free solvent reduces the overall vapor pressure of the electrolyte, which reduces problems with solvent volatility such as outgassing, battery cell bulging, and fire and explosion hazards in the case of flammable organic solvents.

Specific examples of diluted concentrated electrolytes include electrolytes having one or more lithium salts as the active salt, a nonaqueous solvent to dissolve the one or more lithium salts, and one or more fluorine-containing organic compounds as the diluent. The one or more lithium salts may have a concentration in the nonaqueous solvent of at least 3 mols/liter, which is well above the 1-2 mols/liter concentrations of lithium salts in conventional electrolytes for lithium-ion battery cells. The diluent may be incorporated in amounts ranging from, for example, 10 vol. % to 80 vol. % of the total volume of the electrolyte. In many instances, the diluent acts to reduce the viscosity of the highly concentrated lithium salt, and exemplary viscosity ranges for the diluted concentrated electrolytes include 1 cP to 20 cP, which is comparable to the viscosity of a conventional electrolyte for lithium-ion battery cells.

The present technology also includes battery cells that incorporate the diluted concentrated electrolytes. Exemplary battery cells include non-rechargeable, primary battery cells and rechargeable, secondary battery cells. Exemplary battery cells may include a positive electrode, a negative electrode, and the diluted concentrated electrolyte. Specific examples of battery cells include lithium-containing battery cells (e.g., lithium-ion battery cells, lithium-metal battery cells, etc.) having a positive electrode that includes lithium metal or a lithium-containing compound, and a negative electrode that includes at least one of carbon (e.g., graphite), silicon, or a lithium-transition metal oxide (e.g., lithium titanium oxide). Exemplary lithium-containing battery cells have may have one or more enhancements over conventional lithium-ion battery cells that use electrolytes with conventional concentrations of lithium salts (e.g., 1-2 mols/liter). These enhancements may include increased rate capability for the battery cell, increased cycle life for the battery cell, and increased safety for the battery cell, among other enhancements.

Exemplary Diluted Concentrated Electrolytes

Exemplary diluted concentrated electrolytes may include (i) one or more active salts, (ii) a solvent for the active salts, and (iii) a diluent to disperse the dissolved active salts throughout the electrolyte. The active salt is concentrated in the solvent to a point where the amount of free solvent molecules is reduced compared to a conventional, unconcentrated electrolyte where the active salt concentration ranges from 0.5 moles/liter to 2 moles/liter. The increased concentration of the active salt in the solvent is often correlated with an increase in viscosity, which in turn can slow the conductivity of the salt ions in the electrolyte. The diluent can lower the viscosity of the electrolyte by dispersing the concentrated active salt solution into localized regions of highly concentrated solution throughout the electrolyte. The active salt has a significantly lower solubility in the diluent than in the solvent (e.g., at least 10 time less solubility in the diluent than the solvent), which allows the solution of the active salt and solvent to maintain localized regions of high salt concentration in the diluent. This provides a functional distinction between the diluent and the solvent.

Embodiments of the diluted concentrated electrolytes include lithium-salt electrolytes that have one or more lithium salts as the active salts. Exemplary lithium-containing active salts may include one or more lithium fluorosulfonyl imide salts. Specific examples of lithium fluorosulfonyl imide salts include lithium bis(fluorosulfonyl) imide (LiFSI), lithium bis(trifluoromethanesulfonyl) imide (LiTFSI), lithium bis(pentafluoroethanesulfonyl) imide (LiBETI), among other lithium fluorosulfonyl imide salts. Exemplary lithium-containing active salts may include lithium borate salts, such as lithium bis(oxalate)borate (LiBOB), and lithium tetrafluoroborate ($LiBF_4$), among others. Exemplary lithium-containing active salts may include inorganic lithium fluoride salts such as lithium hexafluorophosphate ($LiPF_6$), lithium hexafluoroarsenate ($LiAsF_6$), and lithium tetrafluoroborate ($LiBF_4$), among others. Exemplary lithium-containing active salts may include lithium sulfate, sulfite, and sulfonate salts such as lithium sulfate ($Li_2SO_4$), lithium sulfite ($Li_2SO_3$), and lithium trifluoromethanesulfonate ($LiCF_3SO_3$), among others. Exemplary lithium-containing active salts may include lithium nitrates, nitrites, and thiocyanates such as lithium nitrate ($LiNO_3$), lithium nitrite ($LiNO_2$), and lithium thiocyanate (LiSCN), among others. Exemplary lithium-containing active salts may include lithium halogens and oxyhalogens such as lithium fluoride (LiF), lithium chloride (LiCl), lithium bromide (LiBr), lithium iodide (LiI), and lithium perchlorate ($LiClO_4$), among others.

The lithium-containing active salts may have a concentration in the electrolyte solvent of greater than 3 mols/liter (i.e, greater than 3M). Examples of concentration ranges for the lithium-containing active salt in the electrolyte solvent include 3M to 15M, 4 M to 10 M, 5 M to 8 M, and 6 M to 7 M, among other exemplary ranges. In some embodiments, the lithium-containing active salt may be supersaturated in the electrolyte solvent and have a molar concentration that exceed the conventional saturation concentration for the salt in the solvent at the temperature of the solution. In additional embodiments the lithium-containing active salt solution may be a supersaturated solution at a first, lower temperature of the diluted concentrated electrolyte and may be a saturated or unsaturated solution at a second, higher temperature of the diluted concentrated electrolyte. The first and second temperatures may be within the range of operating temperatures for a battery cell that includes the diluted concentrated electrolyte.

The concentration of the lithium-containing active salt may be selected to minimize the number of free solvent molecules present in the electrolyte. For example, the lithium-containing active salt concentration may be selected to provide a molar ratio with the solvent molecules that incorporates substantially all the solvent molecules into solvent-solute complexes. In some embodiments, the molar ratio of the lithium-containing active salt to the solvent molecules may be about 1:1. In other embodiments, the molar ratio may range from 1:10 to 10:1, 1:5 to 5:1, 1:3 to 3:1, 1:2 to 2:1, or 1:1.1 to 1.1:1, among other molar ratios.

Embodiments of the diluted concentrated electrolytes include lithium-salt electrolytes that have one or more solvents for the lithium active salts. Exemplary solvents include carbonate-containing compounds. Specific examples of carbonate-containing compounds that can be used as solvents in the diluted concentrated electrolytes include ethylene carbonate (EC), vinylene carbonate (VC), propylene carbonate (PC), dimethyl carbonate (DMC), ethyl methyl carbonate (EMC), diethyl carbonate (DEC), methyl acetate (MA), and methyl propionate (MP), among other carbonate-containing compounds. In some embodiments, the solvent does not include fluorinated compounds. In other embodiments, the solvent may include one or more fluorinated carbonate compounds such as monofluoroethylene carbonate (MFEC), difluoroethylene carbonate (DFEC), monfluoromethyl difluoromethyl carbonate (F-DMC), and trifluorodimethyl carbonate (TFDMC).

Embodiments of the diluted concentrated electrolytes include lithium-salt electrolytes that have combinations of two or more solvents for the lithium active salts. For example, embodiments of the electrolyte may include a combination for two carbonate-containing compounds such as ethylene carbonate (EC) and a linear carbonate. Specific examples include ethylene carbonate (EC) and dimethyl carbonate (DMC), ethylene carbonate (EC) and diethyl carbonate (DEC), ethylene carbonate (EC) and ethyl methyl carbonate (EMC), and ethylene carbonate (EC) and propyl methyl carbonate (PMC), among other combinations of ethylene carbonate and a linear carbonate. Embodiments of the solvent also include combinations of three carbonate-containing compounds such as ethylene carbonate (EC), vinylene carbonate (VC), and a linear carbonate. Specific examples include EC/VC/DMC, EC/VC/DEC, EC/VC/EMC, and EC/VC/PMC, among other combinations of ethylene carbonate (EC), vinylene carbonate (VC), and a linear carbonate.

Embodiments of the diluted concentrated electrolytes that have combinations of two or more carbonate solvents may have roughly equal amounts of each carbonate compound, or they may have different amounts of each carbonate compound. For example, a solvent of EC/VC/DMC may have EC ranging from 3 wt. % to 10 wt. % of the solvent (e.g., 5 wt. %), VC ranging from 0.5 wt. % to 2 wt. % of the solvent (e.g., 1 wt. %), and DMC ranging from 88 wt. % to 96 wt. % of the solvent (e.g., 94 wt. %).

The amount of solvent present in the diluted concentrated electrolytes may range from 10 vol. % to 90 vol. %. Exemplary ranges also include 20 vol. % to 90 vol. %, 30 vol. % to 90 vol. %, 40 vol. % to 90 vol. %, 50 vol. % to 90 vol. %, 60 vol. % to 90 vol. %, and 70 vol. % to 90 vol. %, among other ranges. As noted above, the one or more solvents for the lithium-containing active salts may be present in amounts that incorporate substantially all the solvent molecules in solvent-solute complexes with the salts. For example, the majority of the solvent molecules (as a mole percentage of the total number of solvent molecules present in the electrolyte) may be associated (e.g., solvated or coordinated) with the ions of the lithium-containing active salt (e.g., the salt cations) in a range of at least 80 mol. % or more, 85 mol. % or more, 90 mol. % or more, 95 mol. % or more, 96 mol. % or more, 97 mol. % or more, 98 mol. % or more, or 99 mol. % or more, among other ranges. Because the majority of solvent molecules are associated with the ions of the lithium-containing active salt, the mole percentage of free solvent molecules in the electrolyte may be 20 mol. % or less, 15 mol % or less, 10 mol. % or less, 5 mol. % or less, 4 mol. % or less, 3 mol. % or less, 2 mol. % or less, or 1 mol. % or less, among other ranges, as a percentage of the total moles of solvent present in the electrolyte.

Embodiments of the diluted concentrated electrolytes include lithium-salt electrolytes that have one or more diluents for the active salt solutions. Exemplary diluents may provide the following characteristics to the diluted concentrated electrolytes: (i) they lower the viscosity of the electrolyte, (ii) they lower the cost of the electrolyte, (iii) they have permittivity and coordination properties to make a highly soluble dispersion of the concentrated solution of active salt and solvent while not changing the local coordinating environment of the concentrated solution, (iv) they have sufficient inertness and stability to not compromise the electrochemical window of the electrolyte, and (v) they have low flammability and low volatility that do not compromise the safety of the electrolyte in the battery cell.

Exemplary diluents differ from the solvents in their ability to dissolve the lithium-containing active salt. In many instances the ability of dissolve the lithium-containing active salt into its constituent ions is correlated to the polarity of the dissolving medium, as measured by the dielectric constant of the dissolving medium. Exemplary diluents may have a dielectric constant that is lower than the dielectric constant of the solvent. For example, the dielectric constant for the diluent may be 0.5 times or less than the dielectric constant of the solvent. In additional embodiments, the dielectric constant of the diluent may be 0.25 times or less, 0.1 times or less, 0.05 times or less, 0.01 times or less, than the dielectric constant of the solvent. Embodiments include diluents having dielectric constants (c) at 25° C. ranging from 1 to 10.

Exemplary diluents typically have poor solubility or no substantial solubility for the lithium-containing active salt compared to the solvent. For example, the diluent may have a solubility for the lithium-containing active salt that is at least 10 times lower than the solvent, at least 15 times lower, at least 20 times lower, at least 25 times lower, at least 30 times lower, at least 35 times lower, at least 40 times lower, or at least 50 times lower, among other relative solubilities. For a diluent that has a solubility at least 10 times lower than the solvent, a salt having a 10M solubility in the solvent cannot have a solubility greater than 1M in the diluent. Similarly, for a diluent that has a solubility at least 25 times lower than the solvent, a salt having a 10M solubility in the solvent cannot have a solubility greater than 0.25M in the diluent. Exemplary diluents may be selected to have minimal disruption on the solvation structure of the salt-solvent aggregates (e.g., solvation complexes). Exemplary diluents may be selected that have no significant coordination or associate between the diluent molecules and the ions (e.g., cations) of the lithium-containing active salt, and the ions remain associated almost exclusively with the solvent molecules.

Exemplary diluents include organic compounds having one or more substituted fluorine groups. Examples of these fluorinated organic compounds include fluorinated hydrocarbons, fluorinated aromatic compounds, hydrofluoroether compounds, and fluorinated orthoformate compounds, among others. Exemplary fluorinated hydrocarbons include fluorinated linear alkanes having the formula $C_nH_xF_y$, where n=1 to 20, x=0 to 2n+1, y=1 to 2n+2, and x+y=2n+2; fluorinated cycloalkanes having at least one fluorine group; fluorinated alkenes having at least one carbon-carbon double bond and at least one fluorine group; and fluorinated alkynes having at least one carbon-carbon triple bond and at least one fluorine group; among other fluorinated hydrocarbons.

Exemplary fluorinated aromatic compounds include fluorinated benzene compounds having the formula:

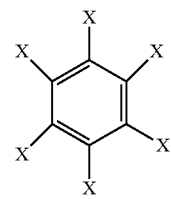

where each X is independently a hydrogen group or a fluorine group, and at least one X is a fluorine group. Specific examples include 1-fluoro-benzene, 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluoro benzene, 1,2,4,5-tetrafluorobenzene, pentafluorobenzene, and hexafluorobenzene. Exemplary fluorinated aromatic compound include fluorinated toluene compounds having the formula:

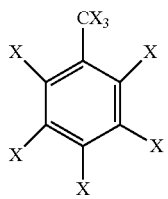

where each X is independently a hydrogen group or a fluorine group, and at least one X is a fluorine group. Specific examples of fluorinated toluene compounds include 1-fluorotoluene (benzomonofluoride), 2-fluorotoluene, 3-fluorotoluene, 4-fluorotoluene, 1,1-difluorotoluene (benzodifluoride), 2,3-difluorotoluene, 2,4-difluorotoluene, 2,5-difluorotoluene, 2,6-difluorotoluene, 1,1,1-trifluorotoluene (benzotrifluoride), 2,3,4-trifluorotoluene, 2,3,5-trifluorotoluene, 2,3,6-trifluorotoluene, and 2,3,4,5-tetrafluorotoluene, among other fluorinated toluene compounds.

Exemplary fluorinated aromatic compound include fluorinated phenyl compounds having the formula:

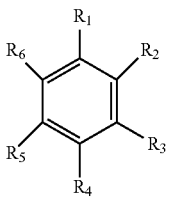

where $R_1$-$R_6$ are each independently, a hydrogen group, a fluorine group, a non-fluorinated $C_1$-$C_6$ alkyl group, or a fluorinated $C_1$-$C_6$ alkyl group, wherein at least one of $R_1$-$R_6$ includes a fluorine group.

Exemplary fluorinated aromatic compounds include fluorinated polyphenolic compounds and fluorinated polycyclic aromatic compounds. Specific examples of fluorinated polyphenolic compounds include fluorinated biphenyl compounds having the formula:

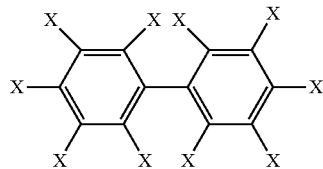

where each X is independently a hydrogen group or a fluorine group, and at least one X is a fluorine group. Embodiments of fluorinated polyphenolic compounds further include one or more X groups representing a non-fluorinated or fluorinated alkyl group. For example one or more X groups may represent a fluorinated or non-fluorinated methyl, ethyl, propyl, butyl, pentyl, or hexyl group. Specific examples of fluorinated polycyclic aromatic compounds include fluorinated naphthalene compounds, fluorinated anthracene compounds, and fluorinated phenantherene compounds having the formulas:

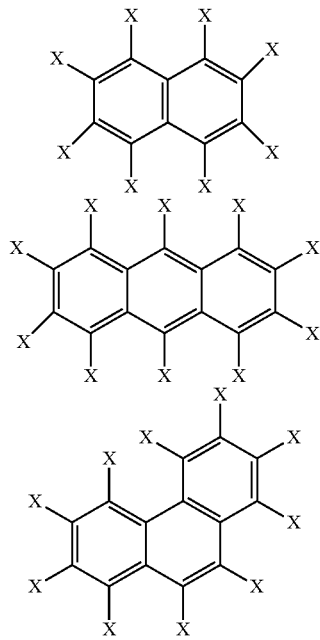

where each X is independently a hydrogen group or a fluorine group, and at least one X is a fluorine group. Embodiments of fluorinated polycyclic aromatic compounds further include one or more X groups representing a non-fluorinated or fluorinated alkyl group. For example one or more X groups may represent a fluorinated or non-fluorinated methyl, ethyl, propyl, butyl, pentyl, or hexyl group.

Exemplary hydrofluoroether compounds include 1,1,2,2-tetrafluoroethyl-2,2,3,3-tetrafluoropropyl ether (HFE), bis(2,2,2-trifluoroethyl) ether (BTFE), 1,1,2,2-tetrafluorethyl-2,2,2-trifluoroethyl ether (TFTFE), methoxynonafluorobutane (MOFB), and ethyoxynonafluorobutane (EOFB), among hydrofluoroether compounds. Exemplary fluorinated orthoformate compounds include tris(2,2,2-trifluoroethyl)orthoformate (TFEO), tris(hexafluoroisopropyl)orthoformate (THFiPO), tris(2,2,-difluoroethyl) orthoformane (TDFEO), bis(2,2,2-trifluoroethyl)methyl orthoformate (BTFEMO), tris(2,2,3,3,3-pentafluoropropyl) orthoformate (TPFPO), and tris(2,2,3,3-tetrafluoropropyl) orthoformate (TTPO), among other fluorinated orthoformate compounds.

The amount of diluent in the diluted concentrated electrolytes may include ranges of 10 vol. % to 90 vol. %, 10 vol. % to 80 vol. %, 10 vol. % to 70 vol. % 10 vol. % to 60 vol. %, 10 vol. % to 50 vol. %, 20 vol. % to 50 vol. % and 30 vol. % to 50 vol. %, among other ranges, as a volume percentage of the total volume of the electrolyte. Exemplary ranges for the amount of diluent in the diluted concentrated electrolytes may include a low end of the range of 10 vol. %, 15 vol. %, 20 vol. %, 25 vol. %, 30 vol. %, 35 vol. %, 40 vol. %, 45 vol. %, and 50 vol. %, and a high end of the range of 90 vol. %, 85 vol. %, 80 vol. %, 75 vol. %, 70 vol. %, 65 vol. %, 60 vol. %, 55 vol. %, and 50 vol. %.

In some embodiments, the diluent reduces the viscosity of the diluted concentrated electrolyte compared to the viscosity of the concentrated solution of the salt and solvent. Exemplary viscosities of diluted concentrated electrolytes include 1 cP (centipoise) to 50 cP, 1 cp to 40 cP, 1 cP to 30 cP, 1 cP to 20 cP, 1 cP to 10 cP, and 1 cP to 5 cP, among other viscosity ranges.

The diluent and solvent in the diluted concentrated electrolytes interact to disperse the salt-solvent solution throughout the electrolyte without substantially lowering the molar concentration of the salt in the solvent. Thus, the diluent disperses localized regions of highly concentrated salt in the solvent throughout the electrolyte. Exemplary molar ratios of the solvent to the diluent in the electrolyte include 1:10 to 10:1, 1:8 to 8:1, 1:7 to 7:1, 1:6 to 6:1, 1:5 to 5:1, 1:4 to 4:1, 1:3 to 3:1, 1:1 to 2:1, and 1:1, among other molar ratio ranges. Exemplary volume ratios of the solvent to the diluent in the electrolyte include 1:10 to 10:1, 1:8 to 8:1, 1:7 to 7:1, 1:6 to 6:1, 1:5 to 5:1, 1:4 to 4:1, 1:3 to 3:1, 1:1 to 2:1, and 1:1, among other volume ratio ranges.

The presence of the diluent in the diluted concentrated electrolytes reduces the overall concentration of the lithium-containing active salts in the electrolyte as a whole. For example, the molar concentration of the lithium-containing active salts in the electrolyte may be at least 20% lower, at least 25% lower, at least 30% lower, at least 35% lower, at least 40% lower, at least 50% lower, at least 60% lower, or at least 70% lower, than the molar concentration of the lithium-containing active salts in the solvent without the diluent. However, because the dissolved lithium-containing active salt is much more coordinated with the solvent than the diluent, several characteristics of the electrolyte more closely correspond to the concentrated salt in the solvent without the diluent. For example the diluted concentrated electrolyte may have ionic conductivity, wettability, and/or solid electrolyte interphase (SEI) layer formation characteristics of the concentrated salt in the solvent without the diluent.

Embodiments of the diluted concentrated electrolytes also include one or more electrolyte additives in the electrolyte. Exemplary electrolyte additives may include negative-electrode additives, positive-electrode additives, redox additives, and flame retardant additives, among other types of additives. Exemplary diluted concentrated electrolytes may include an electrolyte additive in an amount ranging from 0.01 wt. % to 10 wt. % of the total weight of the electrolyte. Additional exemplary concentration ranges for the electrolyte additive include 0.1 wt. % to 5 wt. %, 0.5 wt. % to 5 wt. %, 1 wt. % to 5 wt. %, and 1 wt. % to 3 wt. %, among other concentration ranges for the electrolyte additive as weight percentage of the total weight of the electrolyte.

Exemplary negative-electrode additives include ammonium perfluorocaprylate, and vinyl ethylene carbonate. They also include maleimide compounds such as ortho-maleimide, meta-maleimide, and para-maleimide. They also include glycolide compounds such as glycolide, 3-methyl glycolide, 3,6-dimethyl glycolide, and 3,3,6,6,-tetramethyl glycolide, among other glycolide compounds. Examples also include siloxane compounds such as diethylene glycol methyl-(3-dimethyl(trimethylsiloxy)silyl propyl) ether, diethylene glycol methyl-(3-dimethyl(trimethylsiloxy)silylpropyl)-2-methylpropyl ether, diethylene glycol methyl-(3-bis(trimethylsiloxy)silyl propyl) ether, diethylene glycol-(3-methyl-bis(trimethylsiloxy)silyl-2-methylpropyl) ether, and methyl phenyl bis-methoxydiethoxysilane, among other siloxane compounds. Examples further include olefinic compounds such as vinyl acetate, divinyl adipate, and allyl methyl carbonate, among others. Examples also include sulfur-containing compounds such as ethylene sulfite, propylene sulfite, 1,3-propane sultone, butyl sultone, vinyl ethylene sulfite, prop-1-ene-1,3-sultone, 3-fluoro-1,3-propane sultone, and methylene methanedisulfonate, among other sulfur-containing compounds. Examples further include allyl cyanide, acrylic acid nitrile, p-toluenesulfonyl isocyanate, and ethyl isocyanate. Examples still further include halogen-containing compounds such as chloro-ethylene carbonate, fluoro-ethylene carbonate, α-bromo-γ-butyrolactone, methyl chloroformate, tetrachloroethylene, and 4-fluorophenyl acetate, among other halogen-containing compounds. Examples of anode additives also include (4R, 5R)-dimethyl-2-oxo-1,3,-dioxolane-4,5-dicarboxylate, 2-vinylpyridine, 1,3-propanediolcyclic sulfate, glutaric anhydride, and 3,9-divinyl-2,4,8,10-tetraoxasprio[5,5]undecane.

Exemplary positive-electrode additives include polyphenyl compounds such as biphenyl, o-terphenyl, and m-terphenyl, among other polyphenyl compounds. Examples also include thiophene compounds such as 2,2'-bithiophene, and 2,2":5',2"-terthiophene, among other thiophene compounds. Examples further include furan compounds such as furan, 2-methyl furan, and dimethyl furan, among other furan compounds. Examples also include anisole compounds such as anisole, and thioanisole, among other anisole compounds. Examples further include phosphorous-containing compounds such as triphenyl phosphine, ethyl diphenylphosphinite, tris(pentafluorophenyl)phosphine, and triethyl phosphite, among other phosphorous-containing compounds. Examples further include lithium bis-oxalate compounds such as lithium bis(oxalate)borate, lithium difluoro(oxalato)-borate, and lithium tetrafluoro(oxalate) phosphate, among others. Examples further include N',N-dimethylaniline, N-(triphenylphosphoranylidene) aniline, N,N'-4,4'-diphenylmethane-bismaleimide, 2,2'-bis[4-[4-maleimidophenoxy)phenyl]propane, adamantyl toluene, tris(pentafluorophenyl)borane, and 3,4-ethylenedioxythiophene, among other examples of positive-electrode additives. Examples still further include fluorinated carbonates such as 4-(trifluoromethyl) ethylene carbonate, 4-(perfluorobutyl) ethylene carbonate, 4-(perfluorohexyl) ethylene carbonate, and 4-(perfluorooctyl) ethylene carbonate, among other fluorinated carbonates. Examples further include trimethoxyboroxine, succino nitrile, tris(trimethylsilyl)phosphite, trimethylene sulfate, triphenylamine, 1,4-benzodiozane-6,7-diol, 1,2,3-dioxathiolane-2,2-dioxide, di-(2,2,2-trifluoroethyl)carbonate, tris(trimethylsilyl)borate, tris(trimethylsilyl)phosphate, 1,3,5-trihydroxybenzene, tetraethoxysilane, N,N-diethylamino trimethylsilane, and trimethyl borate, among other positive-electrode additives.

Exemplary redox additives include 2,5-di-tert-butyl-1,4-dimethoxybenzene, 3,5-di-tert-butyl-1,2,-dimethoxybenzene, 4,6-tert-butyl-1,3-benzodioxole, 5,7-tert-butyl-1,4-benzodioxin, 4-tert-butyl-1,2-dimethoxybenzene, 1,4-di-tert-butyl-2,5-bis(2,2,2-trifluoroethoxybenzene), tetraethyl-2,5-di-tert-butyl-1,4-phenylene diphosphate, dimethoxydiphenylsilane, 1,4-bis[bis(1-methylethyl)phosphinyl]-2,5-dimethoxybenzene, 1,4-bis(trimethylsilyl)-2,5-dimethoxybenzene, 2-(pentafluorophenyl)-tetrafluoro-1,3,2-benzodioxaborole, tris(4-bromophenyl) amine, tris(2,4-dibromophenyl) amine, diphenyl amine, triphenylamine, and ferrocene, among other redox additives. Exemplary redox additives also include TEMPO compounds such as 2,2,6,6-tetramethylpiperinyl-oxide, 4-methoxy-TEMPO, 4-cyano-TEMPO, and 3-cyano-2,2,5,5-tetramethyl-1-pyrrolidinyloxy, among other TEMPO compounds. Exemplary redox additives further include phenothiazine compounds such as phenothiazine, 10-methyl-phenothiazine, 10-ethylphenothiazine, 3-chloro-10-methylphenothiazine, 10-isopropylphenothiazine, 10-acetylphenothiazine, N-isopropylphenothiazine, N-tert-butylphenothiazine, and N-phenylphenothiazine, among other phenothiazine compounds.

Exemplary flame retardant additives include organic phosphorous compounds such as dimethyl methylphosphonate, diethylethylphosphonate, triphenyl phosphate, tri-(4-methoxyphenyl) phosphate, cresyl diphenyl phosphate, diphenyloctyl phosphate, bis(2-methoxyethoxy)methyl allylphosphonate, triethoxyphsphazen-N-phosphoryldiethylester, (ethoxy)pentafluorocyclotriphosphazene, bis(2,2,2-trifluoroethyl)methylphosphonate, triphenyl phosphite, bis(2,2,2-trifluoroethyl)ethylphosphonate, resorcinol bis(diphenyl phosphate), bis(N,N-diethyl)(2-methoxyethoxy)methylphosphonamidate, ethylene ethyl phosphate, triethyl phosphate, phosphaphenanthrene, and 1-butyl-1-methylpyrrolidinium hexafluorophosphate, among other organic phosphorous compounds. Exemplary flame retardant additives may also include fluorine-containing compounds such as allyl tris(2,2,2-trofluoroethyl)carbonate, and 2,4,6-tris(trifluoromethyl)-1,3,5-triazine, among other fluorine-containing flame retardant compounds.

Exemplary Effects of Diluted Concentrated Electrolytes on Battery Cell Performance The above-described diluted concentrated electrolytes can affect many different battery cell performance characteristics including the rate capability of the battery cell, the cycle life of the battery cell, and the internal electrical resistance of the battery cell, among other performance characteristics. The rate capability of the battery cell may be evaluated by comparing the discharge capacity retention, typically measured as a percentage of the battery cell's initial discharge capacity, at two or more different charge and/or discharge rates, typically described as a multiple of the C-Rate. The cycle life of the battery cell may be evaluated by comparing capacity retention over a range of charging and discharging cycles for the battery cell. In some comparisons, the cycle lifetime is expressed as the capacity rentention of the battery cell after a fixed number of charge/discharge cycles (e.g., 20 cycles, 50 cycles, 60 cycles, 100 cycles, 200 cycles, 300 cycles, 500 cycles etc.). In additional comparisons, the cycle lifetime is expressed as the cycle number where the capacity decreases to 80% of the initial capacity (e.g., 5 cycles, 20 cycles, 50 cycles, 60 cycles, 100 cycles, 200 cycles, 300 cycles, 500 cycles etc.). The internal electrical resistance of the battery cell may be expressed in milliohms (mΩ). The resistance may be measured at a particular battery temperature (e.g., 25° C., 45° C., etc.) and after a particular number of charge/discharge cycles (e.g., Cy 3, Cy 7, Cy 20, Cy 50, etc.).

The diluted concentrated electrolytes can improve the battery cell's performance characteristics relative to a battery cell that includes a conventional electrolyte with a 1-2M concentration of a lithium-containing active salt. The performance improvements may include increasing at least one of the battery cell's rate capability, cycle life, and/or electrical resistance. For example, a battery cell that includes a diluted concentrated electrolyte may have an increased rate capability of at least 10% relative to a battery cell that has a conventional electrolyte but is otherwise identical. Similarly, a battery cell that includes the diluted concentrated electrolyte may have an increased cycle life of at least 10% relative to a battery cell that has a conventional electrolyte but is otherwise identical.

In some embodiments, the diluted concentrated electrolytes can improve (e.g., increase) one or more of the battery cell's performance characteristics by at least 11%, 12%, 13%, 14%, 15%, 16% 17%, 18%, 19%, 20%, 21%, 22%, 23%, 24%, 25%, 30%, 35%, 40%, 45%, 50%, 55%, 60%, 65%, 70%, 80%, and 90%, among other threshold levels. Additional ranges include 10% to 100%, 15% to 90%, 20% to 80%, and 30% to 50%, among other exemplary ranges.

Exemplary Battery Cells

Figure 4:
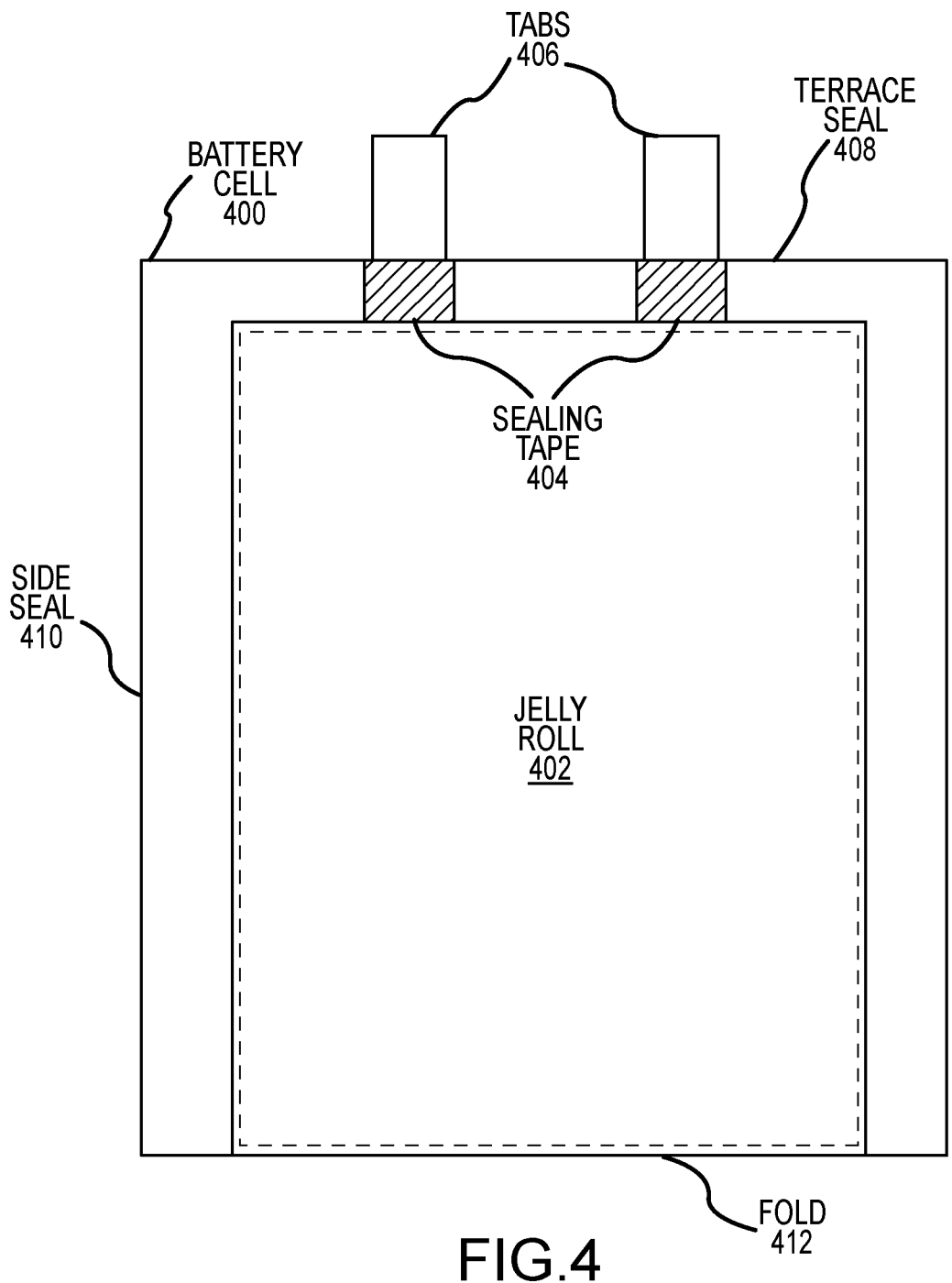
FIG. 4 shows a battery cell in accordance with present embodiments.

FIG. 4 shows a battery cell 400 in accordance with embodiments of the present battery cells that include a diluted concentrated electrolyte. The battery cell 400 may correspond to a lithium-ion battery cell that is used to power a portable electronic device. Battery cell 400 includes a jelly roll 402 containing a number of layers which are wound together, including a positive electrode (a.k.a., cathode) with an active coating, a separator, and a negative electrode (a.k.a., anode) with an active coating. The diluted concentrated electrolyte may surround these layers of the jelly roll 402.

More specifically, jelly roll 402 may include a strip of positive electrode material (e.g., aluminum foil coated with a lithium-containing compound) and a strip of negative electrode material (e.g., copper foil coated with carbon) separated by a strip of separator material (e.g., conducting polymer electrolyte). In the present embodiment, the strips of positive electrode material, negative electrode material, and separator material may be wound to form a spirally wound structure. In other embodiments, strips may be configured to form other types of battery cell structures, such as bi-cell structures.

Exemplary positive electrode materials may include lithium-containing compounds such as lithium cobalt oxide ($LiCoO_2$), lithium nickel manganese cobalt oxide ($LiNi_{1-x-y}Mn_xCo_yO_2$), lithium nickel cobalt aluminum oxide ($LiNi_{0.8}Co_{0.15}Al_{0.05}O_2$), lithium manganese oxide ($LiMn_2O_4$), lithium iron phosphate ($LiFePO_4$), and lithium nickel manganese oxide ($LiNi_{0.5}Mn_{1.5}O_4$), among other positive electrode materials. Exemplary negative electrode materials may include carbon (e.g., graphite), silicon, and mixtures of carbon and silicon, among other negative electrode materials.

During assembly of the battery cell 400, jelly roll 402 may be enclosed in a flexible pouch, which may be formed by folding a flexible sheet along fold line 412. For example, the flexible sheet may be made of aluminum with a polymer film, such as polypropylene and/or polyethylene. After the flexible sheet is folded, the flexible sheet may be sealed, for example, by applying heat along a side seal 410 and along a terrace seal 408. The diluted concentrated electrolyte may be introduced to the flexible pouch before or after it is sealed.

Jelly roll 402 may also include a set of conductive tabs 406 coupled to the positive and negative electrodes. Conductive tabs 406 may extend through seals in the pouch (for example, formed using sealing tape 404) to provide terminals for the battery cell 400. Conductive tabs #06 may then be used to electronically couple battery cell 400 with one or more other battery cells to form a battery pack. For example, the battery pack may be formed by coupling battery cells in series, parallel, or series-and-parallel configurations.

Exemplary Electronic Devices

Figure 5:
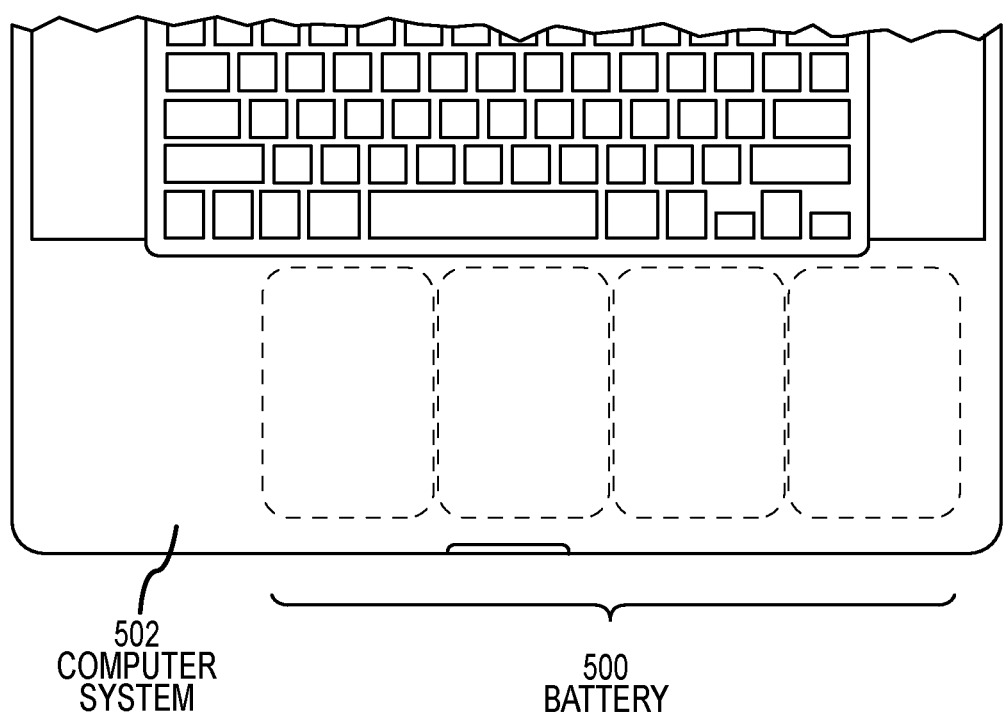
FIG. 5 shows the placement of a battery cell in a computer system in accordance with present embodiments.

FIG. 5 shows the placement of an exemplary battery cell 500 in a computer system 502 in accordance with a present embodiment. Computer system 502 may correspond to a laptop computer, personal digital assistant (PDA), portable media player, mobile phone, digital camera, tablet computer, and/or other portable electronic device. Battery cell 500 may correspond to a lithium-ion battery for the computer system 502 that functions as a power source for computer system 502. For example, battery cell 500 may include one or more lithium-ion battery cells packaged in flexible pouches. The battery cells may then be connected in series and/or parallel and used to power computer systems 502. Each battery cell may include a positive electrode, a negative electrode, a separator, and the present diluted concentrated electrolyte.

Figure 6:
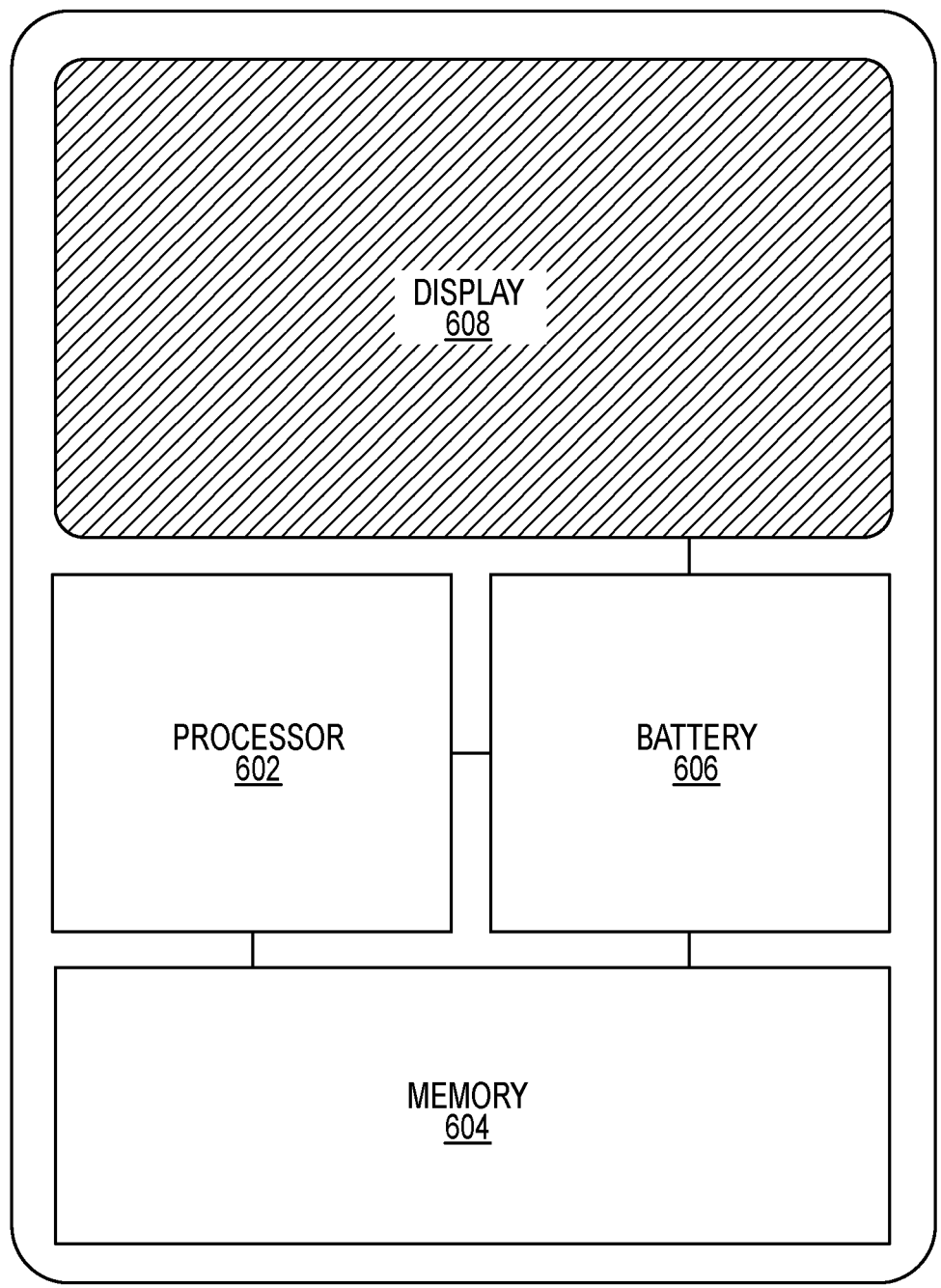
FIG. 6 shows a battery cell in a portable electronic device in accordance with present embodiments.

FIG. 6 shows the placement of the present battery cell 606 for powering a portable electronic device 600 that also includes a processor 602, a memory 604, and a display 608. Portable electronic device 600 may correspond to a laptop computer, mobile phone, PDA, tablet computer, portable media player, digital camera, and/or other type of battery-powered electronic device. Battery cell 606 may be incorporated into a larger battery pack that includes two or more of the battery cells. Each battery cell may include a positive electrode, a negative electrode, a separator, and the present diluted concentrated electrolyte.

Experimental

Rate capability and electrical resistance measurements were taken on lithium-ion battery cells that included the present diluted concentrated electrolytes and compared them with the rate capability and electrical resistance measurements on a lithium-ion battery cell that included a conventional non-aqueous electrolyte. The battery cells were essentially identical except for the electrolytes, and included a lithium-cobalt-oxide (LCO) positive electrode and graphite negative electrode. Table 1 below described the three electrolytes (Ex. #1-3) used in the measurements:

TABLE 1

Composition of Electrolytes in Examples 1-3:

| Example # | Lithium Salt | Li-Salt Conc (mols/liter) | Solvent/ Diluent | Electrolyte Density | Electrolyte Li-ion conductivity | Electrolyte Viscosity |
|---|---|---|---|---|---|---|
| 1 (Comparative) | $LiPF_6$ | 1.15M | EC/PC/DEC/EP[1] | 1.154 g/cc | 8.60 mS/cm | ~5 cP |
| 2 | LiFSI | 6.30M | DMC/EC/VC/FD[2] | 1.366 g/cc | 3.77 mS/cm | 8.6 cP |
| 3 | LiFSI | 7.15M | DMC/EC/VC/FD[2] | 1.371 g/cc | 3.00 mS/cm | 9.6 cP |

[1]EC/PC/DEC/EP = 20/10/20/50 wt. % + VC/PS/FEC/EGPN/HTCN/LiDFOB
[2]DMC/EC/VC/FD = DMC 100% + EC/VC + Fluorinated Diluent (FD)

Figure 7:
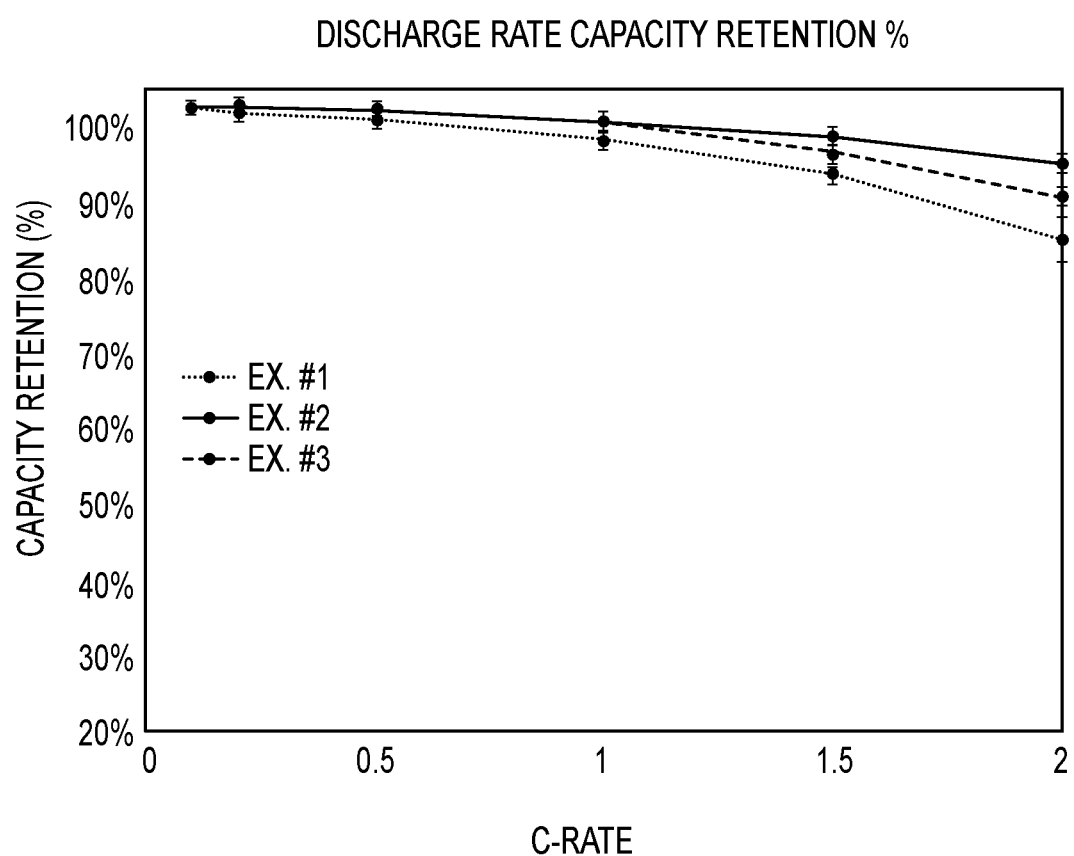
FIG. 7 is a graph of capacity retention as a function of C-Rate for a group of lithium-ion battery cells with various electrolyte formulations.

Rate Capability Measurements:

FIG. 7 is a graph that shows the rate capabilities of the lithium-ion battery cells that incorporate the electrolytes of Examples #1-3. The graph shows the capacity retention versus C-Rate for each of the electrolytes. Capacity retention is measured as a percentage of the initial capacity of the battery cells after seven charge/discharge cycles. The capacity retention is measured following the charging/discharging of the battery cells at six different C-Rates: 0.1C, 0.2C, 0.5C, 1C, 1.5C, and 2C. FIG. 7 shows that the battery cells of Examples #2-3 that included the present diluted concentrated electrolytes had higher rate capabilities across the range of C-Rates measured than the battery cell of Example #1 that included a conventional electrolyte.

Battery Cell Resistance Measurements:

Table 2 below lists the battery cell resistance (DCIR) for the battery cells of Examples #1-3:

TABLE 2

Resistance Measurements (DCIR) for Battery Cells of Examples 1-3:

| Example # | Cell Temperature | DCIR at Cycle #3, 80% DoD |
|---|---|---|
| 1 | 25° C. | 52.4 mΩ |
| 2 | 25° C. | 44.6 mΩ |
| 3 | 25° C. | 50.0 mΩ |

Examples #2-3 that included the present diluted concentrated electrolytes had a lower battery cell resistance (DCIR) than Example #1 that included the conventional electrolyte. This was despite the fact that the electrolytes in Examples #2-3 had lower Li-ion conductivity and higher viscosity than the electrolyte of Example #1.

Figure 8:
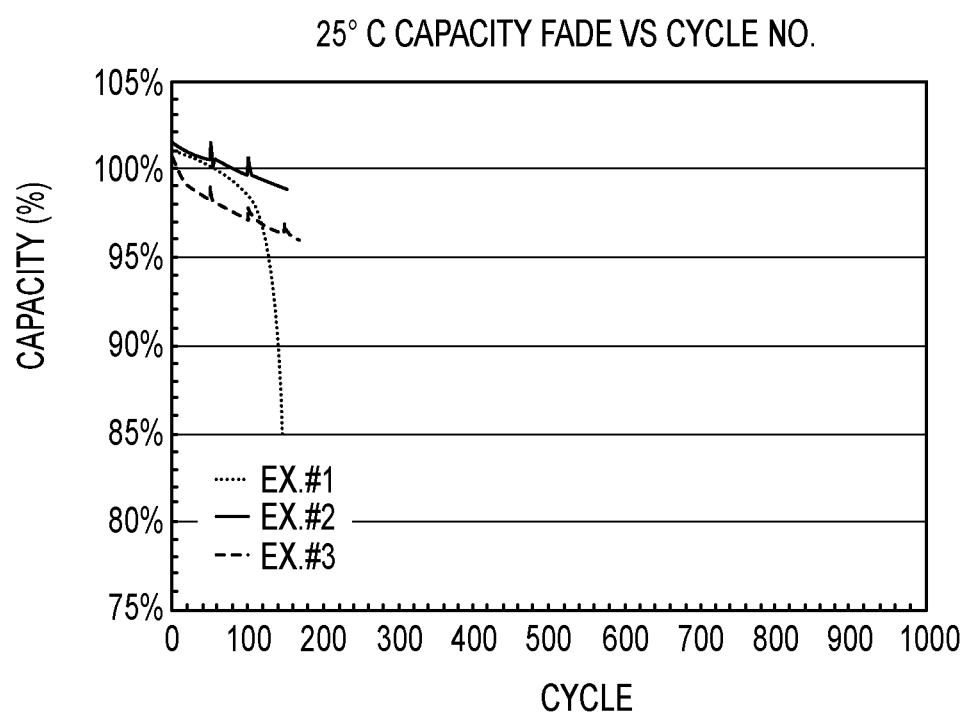
FIG. 8 is a graph of capacity retention as a function of cycle life for a group of lithium-ion battery cells with various electrolyte formulations.

Battery Cell Life Cycle Measurements:

FIG. 8 is a graph that shows the capacity retention as a function of the charge/discharge cycle for the battery cells of Examples #1-3. The graph shows that battery cells of Examples #2-3 which included the present diluted concentrated electrolytes had less of a capacity fade over 150 charge/discharge cycles than the battery cell of Example #1 which included the conventional electrolyte. Thus, these experimental measurements demonstrate that battery cells incorporating the present diluted concentrated electrolytes have higher rate capabilities, lower internal cell electrical resistance, and longer cycle life than battery cells that incorporate conventional, unconcentrated electrolytes.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having disclosed several embodiments, it will be recognized by those of skill in the art that various modifications, alternative constructions, and equivalents may be used without departing from the spirit of the embodiments. Additionally, a number of well-known processes and elements have not been described in order to avoid unnecessarily obscuring the present technology. Accordingly, the above description should not be taken as limiting the scope of the technology.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included. Where multiple values are provided in a list, any range encompassing or based on any of those values is similarly specifically disclosed.

As used herein and in the appended claims, the singular forms "a", "an", and "the" include plural references unless the context clearly dictates otherwise. Thus, for example, reference to "a material" includes a plurality of such materials, and reference to "the cell" includes reference to one or more cells and equivalents thereof known to those skilled in the art, and so forth.

Also, the words "comprise(s)", "comprising", "contain(s)", "containing", "include(s)", and "including", when used in this specification and in the following claims, are intended to specify the presence of stated features, integers, components, or operations, but they do not preclude the presence or addition of one or more other features, integers, components, operations, acts, or groups.

What is claimed is:

1. An electrolyte for a lithium-containing battery cell, the electrolyte comprising:
   a solvent comprising at least one carbonate ester;
   at least one lithium salt having a concentration ranging from 4 mol/liter to 10 mol/liter in the solvent;
   a diluent comprising an aromatic fluorocarbon;
   a first additive comprising a lithium-free sulfonate or sultone compound; and
   a second additive comprising a C—N containing compound,
   wherein the electrolyte has a viscosity ranging from 1 cP to 20 cP, and
   wherein the aromatic fluorocarbon comprises a fluorinated polyphenolic compound, a fluorinated polycyclic aromatic compound, 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluorobenzene, 1,2,3,5-tetrafluorobenzene, 1,2,4,5-tetrafluorobenzene, pentafluorobenzene, hexafluorobenzene, 2-fluorotoluene, 3-fluorotoluene, 4-fluorotoluene, 2,3-difluorotoluene, 2,4-difluorotoluene, 2,5-difluorotoluene, 2,6-difluorotoluene, 3,4-difluorotoluene, 2-fluorobenzotrifluoride, 3-fluorobenzotrifluoride, 4-fluorobenzotrifluoride, 3-fluoro-o-xylene, 4-fluoro-o-xylene, 2-fluoro-m-xylene, 5-fluoro-m-xylene, 2-methylbenzotrifluoride, 3-methylbenzotrifluoride, 4-methylbenzotrifluoride, or octafluorotoluene.

2. The electrolyte of claim 1, wherein the concentration of the at least one lithium salt ranges from 6 mol/liter to 7 mol/liter in the solvent.

3. The electrolyte of claim 1, wherein the at least one lithium salt is supersaturated in the solvent.

4. The electrolyte of claim 1, wherein the at least one lithium salt comprises a carbon-containing lithium salt.

5. The electrolyte of claim 1, wherein the at least one lithium salt comprises $LiPF_6$, $LiAsF_6$, $LiBF_4$, $LiSbF_6$, $LiAlCl_4$, $LiClO_4$, $LiBrO_4$, $LiIO_4$, or a combination of these.

6. The electrolyte of claim 1, wherein the at least one lithium salt comprises $LiCF_3SO_3$, $LiC_4F_9SO_3$, $LiCF_3COO$, $LiN(CF_3CO)_2$, $LiN(CF_3SO_2)_2$, $LiN(C_2F_5SO_2)_2$, $LiN(CF_3SO_2)(C_4F_9SO_2)$, $LiC(CF_3SO_2)_3$, $LiN(SO_2F)_2$, $LiPF_4(CF_3)$, $LiPF_4(C_2F_5)$, $LiPF_4(CF_3SO_2)_2$, $LiPF_4(C_2F_5SO_2)_2$, $LiBF_2(C_2F_5SO_2)_2$, or a combination of these.

7. The electrolyte of claim 1, wherein the carbonate ester comprises one or both of a linear carbonate ester or a cyclic carbonate ester.

8. The electrolyte of claim 7, wherein the linear carbonate ester comprises dimethyl carbonate, diethyl carbonate, dipropyl carbonate, methyl ethyl carbonate, methyl propyl carbonate, ethyl propyl carbonate, or a combination of these.

9. The electrolyte of claim 7, wherein the cyclic carbonate ester comprises ethylene carbonate, propylene carbonate, or vinylene carbonate.

10. The electrolyte of claim 1, wherein the aromatic fluorocarbon represents 10% to 80% by volume of the electrolyte.

11. The electrolyte of claim 1, wherein the C—N containing compound is an isocyanate.

12. The electrolyte of claim 1, further comprising a third additive comprising a phosphorous-containing compound.

13. The electrolyte of claim 1, wherein the electrolyte has a viscosity ranging from 1 cP to 10 cP.

14. The electrolyte of claim 1, wherein the electrolyte further comprises a redox additive.

15. A lithium-containing battery cell comprising:
    a positive electrode;
    a negative electrode; and
    a lithium-containing electrolyte, wherein the lithium-containing electrolyte comprises:
    a solvent comprising at least one carbonate ester;
    at least one lithium salt having a concentration ranging from 3 mol/liter to 15 mol/liter in the solvent, wherein the at least one lithium salt is supersaturated in the solvent;
    a diluent comprising an aromatic fluorocarbon;
    a first additive comprising a lithium-free sulfonate or sultone compound; and
    a second additive comprising a C—N containing compound,
    wherein the lithium-containing electrolyte has a viscosity ranging from 1 cP to 20 cP, and
    wherein the aromatic fluorocarbon comprises a fluorinated polyphenolic compound, a fluorinated polycyclic aromatic compound, 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluorobenzene, 1,2,3,5-tetrafluorobenzene, 1,2,4,5-tetrafluorobenzene, pentafluorobenzene, hexafluorobenzene, 2-fluorotoluene, 3-fluorotoluene, 4-fluorotoluene, 2,3-difluorotoluene, 2,4-difluorotoluene, 2,5-difluorotoluene, 2,6-difluorotoluene, 3,4-difluorotoluene, 2-fluorobenzotrifluoride, 3-fluorobenzotrifluoride, 4-fluorobenzotrifluoride, 3-fluoro-o-xylene, 4-fluoro-o-xylene, 2-fluoro-m-xylene, 5-fluoro-m-xylene, 2-methylbenzotrifluoride, 3-methylbenzotrifluoride, 4-methylbenzotrifluoride, or octafluorotoluene.

16. The lithium-containing battery cell of claim 15, wherein the positive electrode comprises lithium metal, one or more lithium-transition metal compounds, or a combination of these.

17. The lithium-containing battery cell of claim 16, wherein the one or more lithium-transition metal compounds comprise lithium cobalt oxide, lithium manganese oxide, lithium iron phosphate, lithium nickel oxide, lithium nickel manganese cobalt oxide, or lithium nickel cobalt aluminum oxide.

18. The lithium-containing battery cell of claim 15, wherein the negative electrode comprises graphite, silicon, lithium titanium oxide, or a combination of these.

19. The lithium-containing battery cell of claim 15, wherein the lithium salt in the lithium-containing electrolyte comprises $LiPF_6$, $LiAsF_6$, $LiBF_4$, $LiSbF_6$, $LiAlCl_4$, $LiClO_4$, $LiBrO_4$, $LiIO_4$, $LiCF_3SO_3$, $LiC_4F_9SO_3$, $LiCF_3COO$, $LiN(CF_3CO)_2$, $LiN(CF_3SO_2)_2$, $LiN(C_2F_5SO_2)_2$, $LiN(CF_3SO_2)(C_4F_9SO_2)$, $LiC(CF_3SO_2)_3$, $LiN(SO_2F)_2$, $LiPF_4(CF_3)$, $LiPF_4(C_2F_5)$, $LiPF_4(CF_3SO_2)_2$, $LiPF_4(C_2F_5SO_2)_2$, $LiBF_2(C_2F_5SO_2)_2$, or a combination of these.

20. The lithium-containing battery cell of claim 15, wherein the electrolyte further comprises a redox additive.

* * * * *